US006896682B1

(12) United States Patent
McClellan et al.

(10) Patent No.: US 6,896,682 B1
(45) Date of Patent: May 24, 2005

(54) METHOD AND SYSTEM FOR INTERNAL LIGATION OF TUBULAR STRUCTURES

(75) Inventors: Scott B. McClellan, Heber City, UT (US); Patricia M. Moulis, Salt Lake City, UT (US); Annette M. L. McClellan, Heber City, UT (US); Thomas G. Taylor, Salt Lake City, UT (US); David L. Wells, Salt Lake City, UT (US)

(73) Assignee: Biomedical Engineering Solutions, Inc., Salt Lake City, UT (US)

( * ) Notice: Subject to any disclaimer, the term of this patent is extended or adjusted under 35 U.S.C. 154(b) by 852 days.

(21) Appl. No.: 09/712,408

(22) Filed: Nov. 14, 2000

(51) Int. Cl.[7] ............................................. A61B 17/10
(52) U.S. Cl. ........................ 606/140; 606/141; 606/144
(58) Field of Search ................................. 606/140, 141, 606/139, 144, 151, 157, 158, 142, 32, 40; 128/831

(56) References Cited

U.S. PATENT DOCUMENTS

| | | | |
|---|---|---|---|
| 3,635,223 A | * | 1/1972 | Klieman ..................... 606/194 |
| 3,870,048 A | | 3/1975 | Yoon |
| 3,911,923 A | | 10/1975 | Yoon |
| 3,967,625 A | | 7/1976 | Yoon |
| 3,989,049 A | | 11/1976 | Yoon |
| 4,245,623 A | | 1/1981 | Erb |
| 4,374,523 A | | 2/1983 | Yoon |
| 4,493,319 A | | 1/1985 | Polk et al. |
| 4,606,336 A | | 8/1986 | Zeluff |
| 4,700,701 A | | 10/1987 | Montaldi |
| 5,095,917 A | | 3/1992 | Vancaillie |
| 5,224,497 A | * | 7/1993 | Ehlers ........................ 128/898 |
| 5,290,284 A | | 3/1994 | Adair |
| 5,303,719 A | | 4/1994 | Wilk et al. |
| 5,320,630 A | | 6/1994 | Ahmed |
| 5,591,177 A | | 1/1997 | Lehrer |
| 5,653,690 A | * | 8/1997 | Booth et al. ........... 604/103.07 |
| 5,709,224 A | | 1/1998 | Behl et al. |
| 5,746,692 A | | 5/1998 | Bacich et al. |
| 5,776,141 A | | 7/1998 | Klein et al. |
| 5,788,715 A | | 8/1998 | Watson, Jr. et al. |
| 5,788,716 A | | 8/1998 | Kobren et al. |
| 5,792,153 A | | 8/1998 | Swain et al. |
| 5,797,952 A | | 8/1998 | Klein |
| 5,807,236 A | | 9/1998 | Bacich et al. |
| 5,807,239 A | | 9/1998 | DiBernardo |
| 5,826,584 A | | 10/1998 | Schmitt |
| 5,843,121 A | | 12/1998 | Yoon |
| 5,846,255 A | | 12/1998 | Casey |
| 5,868,760 A | | 2/1999 | McGuckin, Jr. |
| 5,871,475 A | | 2/1999 | Frassica |
| 5,873,815 A | | 2/1999 | Kerin et al. |
| 5,885,258 A | | 3/1999 | Sachdeva et al. |
| 5,895,412 A | | 4/1999 | Tucker |
| 5,908,429 A | | 6/1999 | Yoon |

(Continued)

OTHER PUBLICATIONS

PCT International Search Report, PCT/US01/43937, dated Jul. 3, 2002.

*Primary Examiner*—Henry Bennett
*Assistant Examiner*—Kathryn Odland
(74) *Attorney, Agent, or Firm*—TraskBritt

(57) ABSTRACT

A surgical device for performing internal ligation of a fallopian tube or other tubular anatomical structure, by application of one or more ligating bands to a folded portion of the wall of the tubular structure. Also the invention includes a method of using the device. The inventive method and device may be used for sterilization to prevent undesired pregnancies, or for other medical applications. The device includes an elongated tubular element that is inserted into the fallopian tube; a grasper that extends out of the tubular element, grasps the interior of the fallopian tube and retracts into the tubular element drawing in a folded bundle of the fallopian tube tissue; and a pusher balloon for pushing a ligating band from the tip of the tubular element onto the tissue bundle.

14 Claims, 15 Drawing Sheets

U.S. PATENT DOCUMENTS

| | | |
|---|---|---|
| 5,921,993 A | 7/1999 | Yoon |
| 5,935,056 A | 8/1999 | Kerin et al. |
| 5,935,098 A | 8/1999 | Blaisdell et al. |
| 5,935,137 A | 8/1999 | Saadat et al. |
| 5,954,715 A | 9/1999 | Harrington et al. |
| 5,957,936 A | 9/1999 | Yoon et al. |
| 5,989,580 A | 11/1999 | Wallace et al. |
| 6,007,551 A | 12/1999 | Peifer et al. |
| 6,019,757 A | 2/2000 | Scheldrup |
| 6,042,590 A | 3/2000 | Sporri et al. |
| 6,042,591 A | 3/2000 | Mears |
| 6,059,797 A | 5/2000 | Mears |
| 6,066,139 A | 5/2000 | Ryan et al. |
| 6,066,147 A | 5/2000 | Mears |
| 6,068,626 A | 5/2000 | Harrington et al. |
| 6,077,289 A * | 6/2000 | Mollenauer .................. 606/192 |
| 6,231,561 B1 * | 5/2001 | Frazier et al. .............. 604/500 |
| 6,558,400 B2 * | 5/2003 | Deem et al. ................. 606/151 |
| 6,626,930 B1 * | 9/2003 | Allen et al. .................. 606/213 |
| 6,629,534 B1 * | 10/2003 | St. Goar et al. ............ 128/898 |
| 2003/0158563 A1 * | 8/2003 | McClellan et al. ......... 606/151 |

* cited by examiner

METHOD AND SYSTEM FOR INTERNAL LIGATION OF TUBULAR STRUCTURES

BACKGROUND OF THE INVENTION

Technical Field: The present invention relates to methods for blocking tubular anatomical structures. In particular, the present invention relates to methods for ligating the fallopian tube to achieve sterilization. The present invention pertains in addition to devices for performing tubal ligations.

Occlusion of tubular anatomical structures is desirable for various medical treatments. One important application of occlusion techniques is blockage of the fallopian tubes in the female or vas deferens in the male to achieve sterilization and prevent undesired pregnancies.

Various methods for producing occlusion or blockage of tubular anatomical structures have been considered for contraceptive purposes. A commonly used method for blocking the fallopian tube is to tie off or clamp the fallopian tube. The tube may be tied in two locations and the intermediate portion of tube removed. A similar result may be obtained by grasping and folding over a portion of the tube and tying off a loop of tube that does not communicate with the remainder of the tube. The folded segment of tube may be blocked by a loop of suture material, a elastic ligating band or O-ring, or a clamp. Access to the fallopian tube is usually gained through endoscopic surgery, either through the abdominal wall or, less commonly, through the wall of the vagina. Such methods are less invasive than conventional surgical methods, but still have an undesirably high risk of infection and tissue damage, and are accompanied by an undesirable recovery time and level of discomfort.

In order to eliminate the need for endoscopic or other, more invasive, surgery, a number of approaches have been devised for blocking the lumen of the fallopian tube after accessing the interior of the fallopian tube by inserting a catheter into the lumen of the tube via the vagina and uterus.

One approach is to block the fallopian tube by injecting an adhesive or sealant, typically a polymeric material, into the fallopian tube to form a plug. Another approach is to insert a pre-formed occlusive device or plug into the lumen of the fallopian tube or the utero-tubal junction. However, either type of plug may separate or dislodge from the wall of the fallopian tube, resulting in unreliable or impermanent blockage.

Another approach for blocking the fallopian tube or other tubular anatomic structures is to induce the formation of sclerosis or scar tissue to block the tube. Tissue damage may be induced chemically or thermally. However, this method is relatively difficult to accomplish successfully and requires skilled personnel and specialized equipment, making it unsuited for use in certain settings.

SUMMARY OF THE INVENTION

One object of the invention is to provide a method and system for applying a ligating structure to the interior of a tubular anatomical structure.

Another object of the invention is to produce a reliable occlusion of a tubular anatomical structure. Yet another object of the invention is to produce occlusion of a tubular anatomical structure that is also permanent.

Yet another object of the invention is to provide an inexpensive method for occluding a tubular anatomical structure.

A further object of the invention is to provide a partially or completely disposable device for performing occlusion of a tubular anatomical structure.

Another object of the invention is to provide a method for performing tubal ligations which requires only minimally invasive surgery, thereby reducing damage to vascular and reproductive tissues and reducing post-surgical discomfort and recovery time.

Another object of the invention is to provide a method for performing tubal ligations which may reduce the risk of infection.

To achieve the foregoing objects, and in accordance with the invention as embodied and broadly described herein, a device is provided for applying ligating bands to tissue in the interior of a tubular anatomical structure. The invention also includes a method of using the device.

The device is a surgical instrument having a proximal and a distal end, the device being generally elongated and configured to permit insertion of the distal end into a fallopian tube via the vagina and uterus, while the device is held and controlled external to the patient, at the proximal end.

The device includes an elongated tubular element having a central, longitudinally extending lumen and a grasper slidably disposed in the lumen. The grasper is capable of being extended out of the distal end of the tube, grasping tissue on the interior of the fallopian tube, and retracting back into the inner tube with the grasped tissue. One or more ligating bands are held on the distal end of the tube. Ligating bands are released from the distal end of the tube to contract about the grasped tissue. The proximal end of the device is provided with a handle or base, and a number of controls thereon for controlling extension and retraction of grasper with respect to the tube and release of ligating bands onto the grasped tissue. The device may be provided with a current source for supplying current to cauterize tissue held by the grasper. The device may also be provided with an additional lumen for delivering drugs or other compounds, such as antibiotics, topical anesthetics, or chemical cauterizing agents, in the vicinity of the ligation.

The method of using the device includes the steps of inserting the distal end of the device into a tubular anatomical structure, causing the grasper to extend out of the tube, grasping tissue in the interior of the tubular anatomical structure with the grasper, retracting the grasper into the lumen of the inner tube, drawing grasped tissue into the distal end of tube to form an inner tissue bundle, and releasing a ligating band from the distal end of the tube to contract around the inner tissue bundle. The method may include the further steps of withdrawing the device to a new position within the tubular anatomical structure and repeating the preceding steps to apply one or more additional ligating bands.

DETAILED DESCRIPTION OF THE INVENTION

Figure 1:
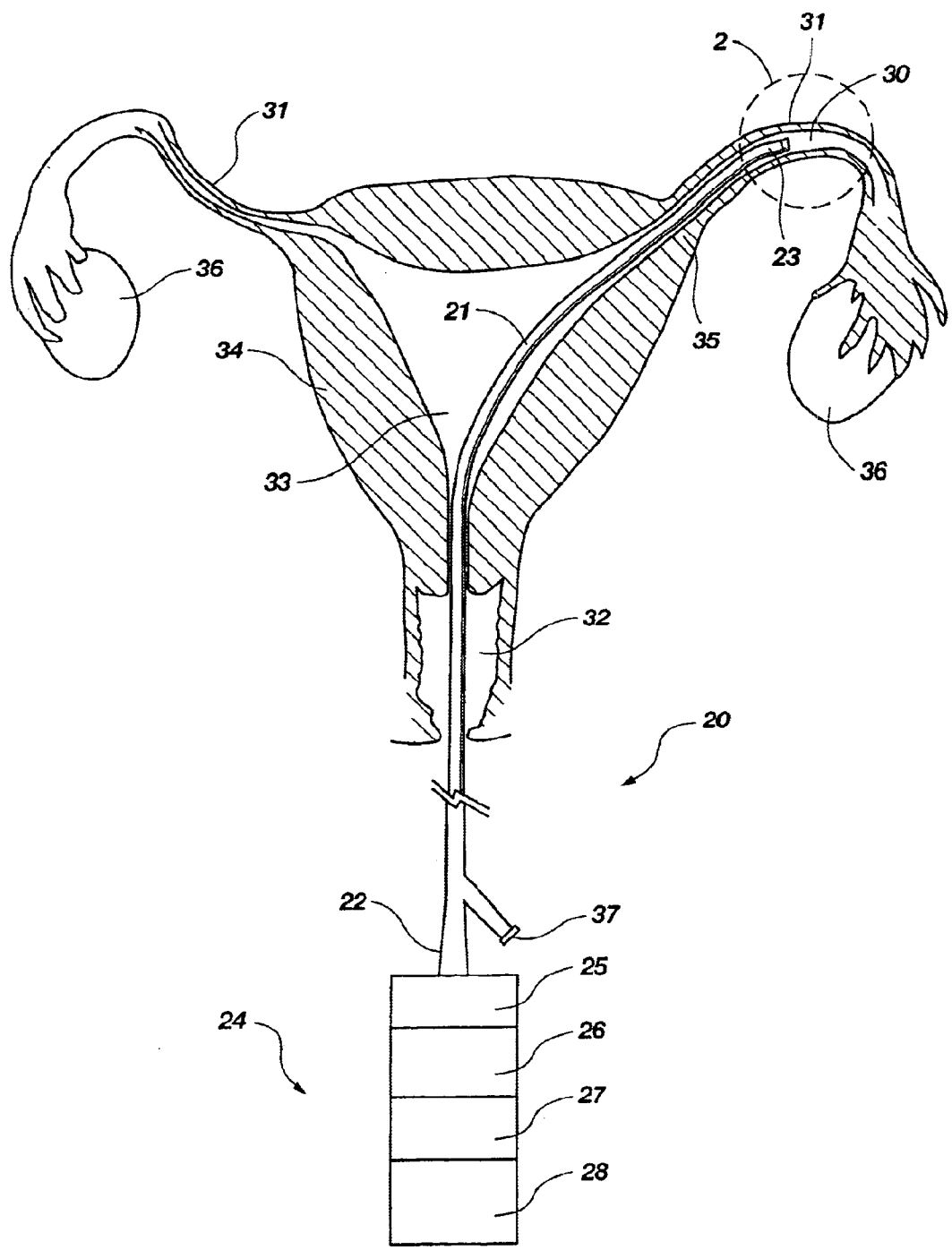
FIG. 1 is a view of an embodiment of the device inserted into the fallopian tube of a patient, with the controls for the device shown in schematic form.

FIG. 1 depicts the inventive device for performing internal ligation of tubular structures. Device 20 includes an elongated tubular element 21 having a proximal end 22 and distal end 23. Proximal end 22 of tubular element 21 is connected to control segment 24, which includes controls 25, 26, 27, and 28 for controlling the device, and which also is used for supporting the device during use. Control segment 24 may be configured as a handle to be held in the hand of a person using device 20, or may be configured for mounting on an examination table or other base. Device 20 is supported and controlled by control segment 24 while distal end 23 is inserted into the lumen 30 of fallopian tube 31 of a patient via the vagina 32, lumen 33 of uterus 34, and uterine horn 35. Ovaries 36 are also shown in FIG. 1. Proximal end 22 may include an access port 37 to permit injection of anesthetics, antibiotics, or other substances into tubular element 21 for infusion into the fallopian tube in the vicinity of the ligation.

Figure 2:
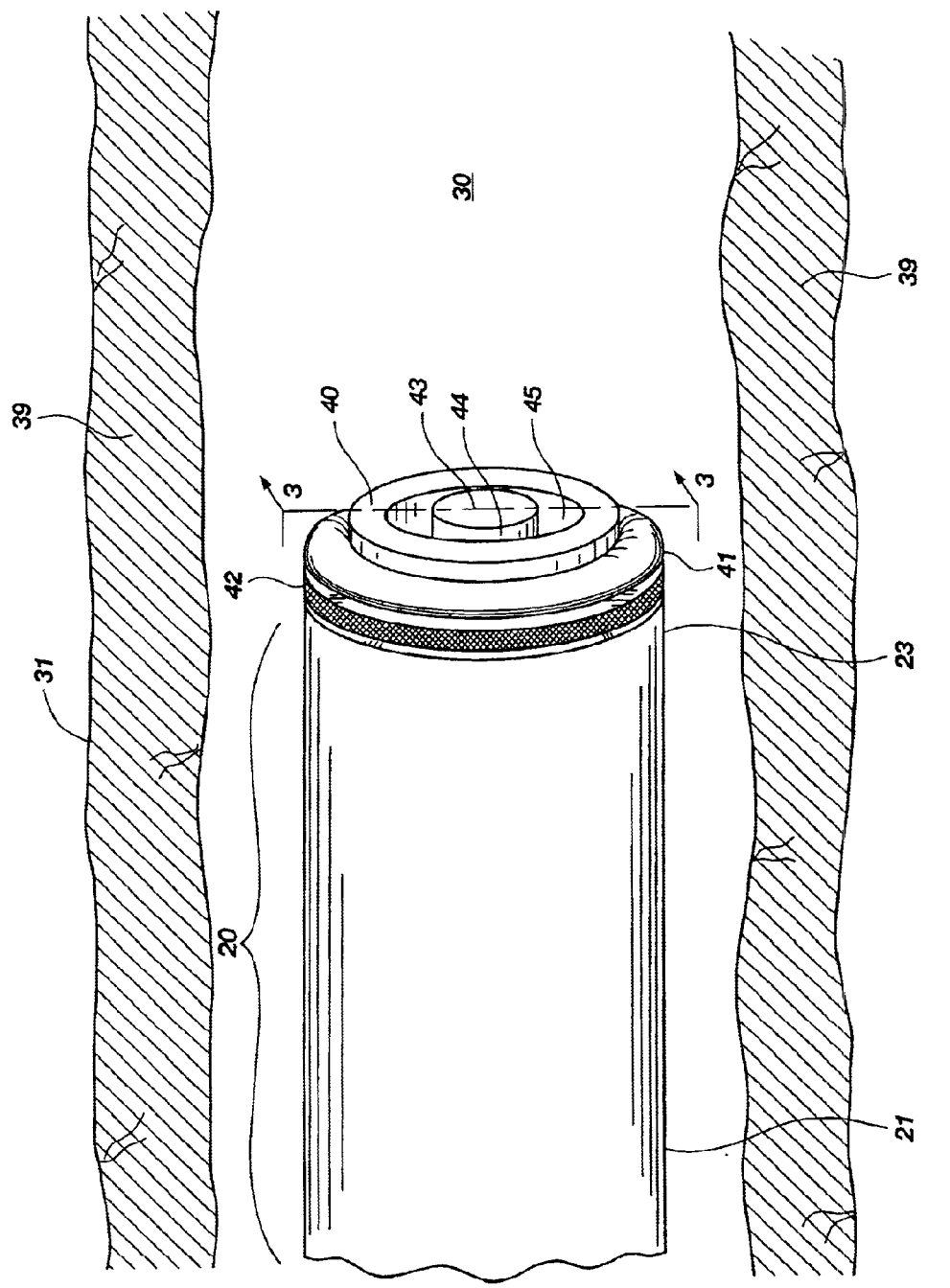
FIG. 2 is a perspective view of an embodiment of the device positioned in a fallopian tube, with the grasper shaft unextended.

FIG. 2 shows detail of additional components of device 20 at distal end 23 of tubular element 21, from circled region 2 in FIG. 1. Tubular element 21 is shown positioned within the lumen 30 of fallopian tube 31, with the fallopian tube wall 39 shown in cross-section. Distal end 23 of tubular element 21 includes lip 40, on which is held a ligating band 41. Ligating band 41 may be of the type known for use in performing tubal ligations, formed of rubber, silicone, and other suitable materials. Other ligating structures, such as suture loops or clamps, may be used as well. Just proximal to ligating band 41 is pusher 42, which in this example is a pusher balloon having a generally toroidal shape. Pusher balloon 42 can be expanded distally to push ligating band 41 off the distal end 23 of tubular element 21. The distal tip 43 of grasper shaft 44 of grasper 38 (see FIG. 6), is visible in lumen 45 of tubular element 21. Grasper shaft 44 is shown in its unextended position, so that tip 43 does not project significantly beyond the distal end 23 of tubular element 21. Grasper shaft 44 is preferably maintained in an unextended position while device 20 is inserted into the fallopian tube of the patient.

Figure 3:
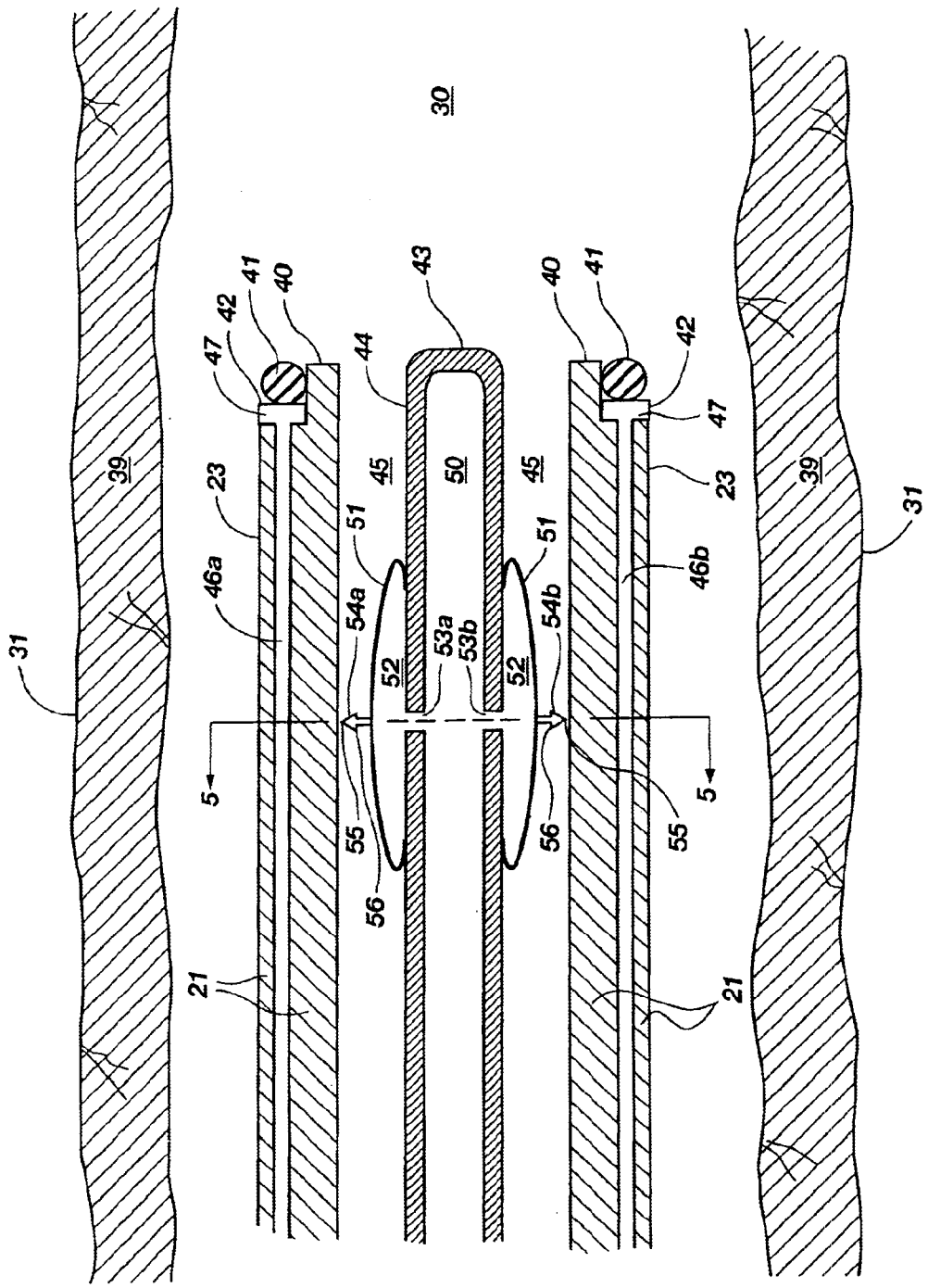
FIG. 3 is a longitudinal cross-sectional view taken along line 3—3 in FIG. 2.

FIG. 3 is a cross-sectional view of device 20 taken along section line 3—3 in FIG. 2. Grasper 38 is slidably disposed in lumen 45 of tubular element 21. In the embodiment of the invention shown here, grasper 38 includes grasper shaft 44, which is hollow with a central lumen 50, and balloon 51, which is attached to grasper shaft 44. Lumen 50 of grasper shaft 44 communicates with the interior 52 of balloon 51 via fluid channels 53a and 53b. In use, balloon 51 is inflated to a selected pressure or volume by the injection of a fluid with a syringe or other pressurized source. In this context, fluid is intended to mean liquids and gases. The fluid in grasper shaft 44 and the interior 52 of balloon 51 could be, for example, air or saline. Balloon 51 may be inflated in the same way as balloon angioplasty catheters. A plurality of barbs, of which only 54a and 54b are visible in the present cross section, are attached to the exterior of balloon 51. Channels 46a and 46b in tubular element 21 communicate with the interior 47 of pusher balloon 42. Air or fluid from a syringe or other pressurized source connected at the proximal ends of channels 46a and 46b is forced into pusher balloon 42 to cause it to expand and push ligating band 41 off of lip 40.

Figure 4:
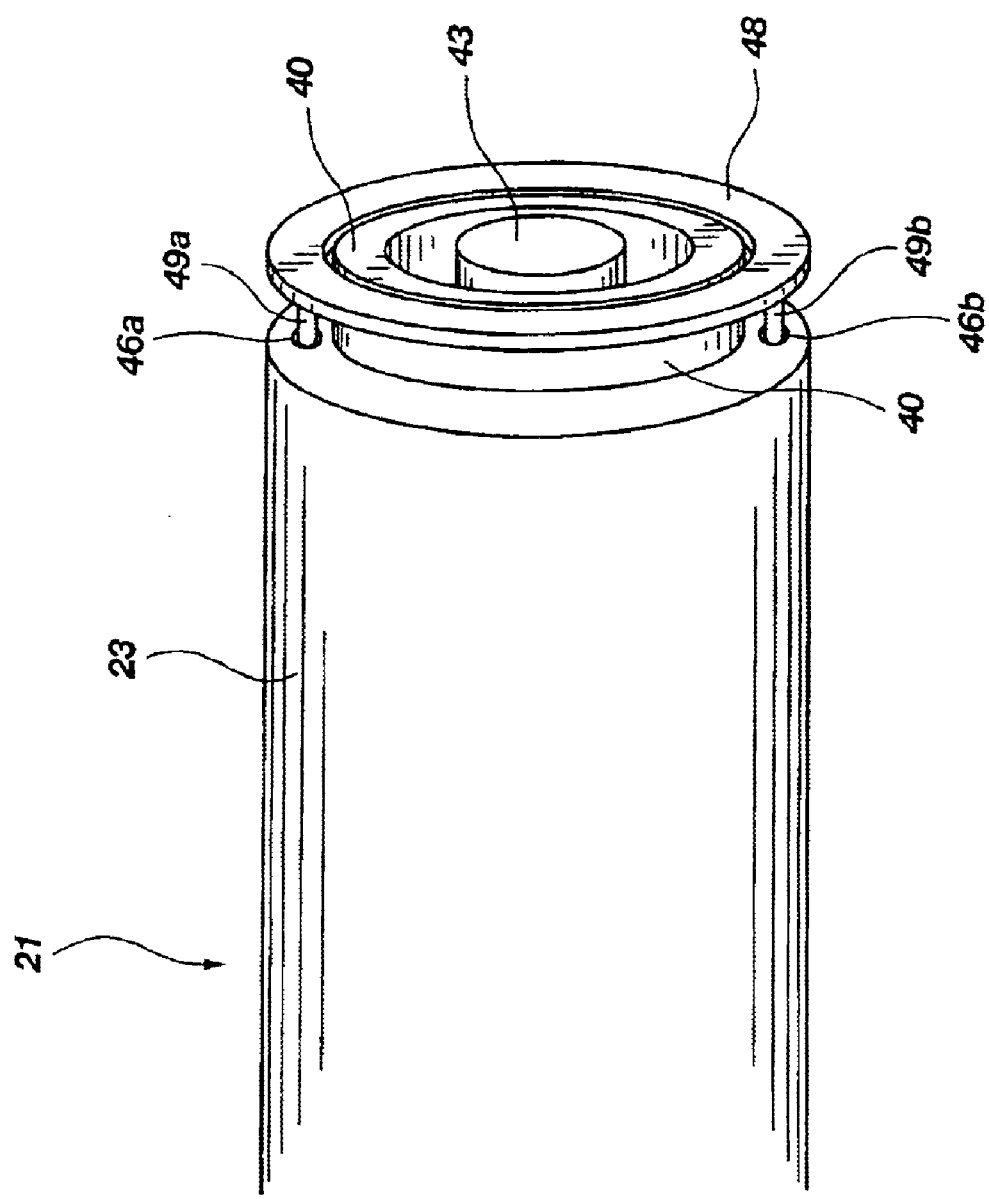
FIG. 4 shows an alternative pusher mechanism for releasing a ligating band.

FIG. 4 depicts an alternative embodiment of the invention in which a pusher disk 48, driven by pusher rods 49a and 49b, is used in place of pusher balloon 42. Pusher rods 49a and 49b are slidably disposed in channels 46a and 46b and are driven by a mechanical actuator (not shown) located at the proximal end of the device, at control segment 24. Various actuation mechanisms may be devised by those of ordinary skill in the art for causing pusher rods 49a and 49b to move pusher disk 48 to push ligating band 41 (not shown) off of lip 40.

Figure 5:
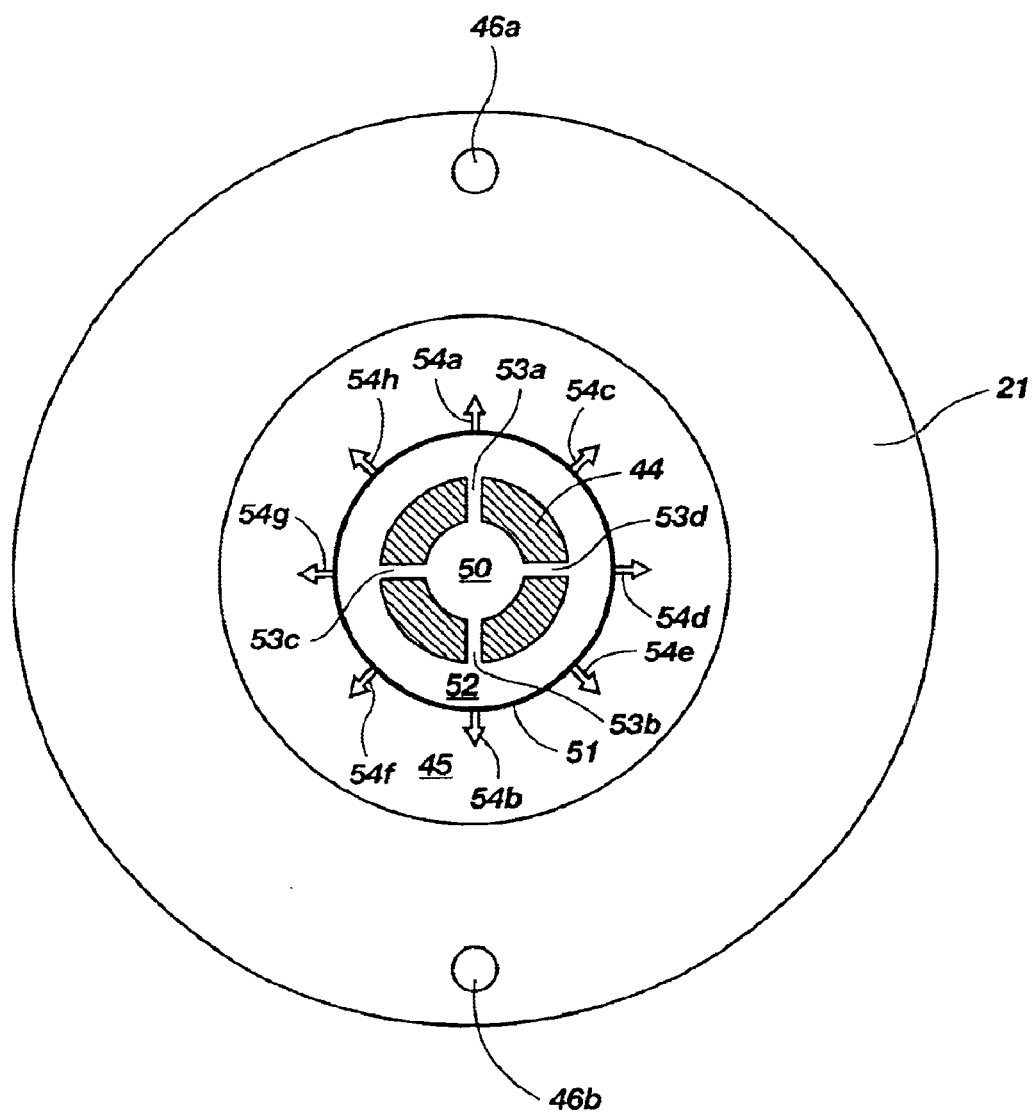
FIG. 5 is a transverse cross sectional view taken along line 5—5 in FIG. 3.

FIG. 5 is a transverse cross section taken at section line 5—5 in FIG. 3. Channels 46a and 46b in tubular element 21 can be seen, as can fluid channels 53a, 53b, 53c, and 53d, which provide fluid communication between grasper shaft lumen 50 and interior 52 of balloon 51. Fluid channels 53c and 53d were not visible in the cross section shown in FIG. 3. Also, all of the plurality of barbs 54a, 54b, 54c, etc., are visible in this cross section. Although two channels 46a and 46b and four fluid channels 53a, 53b, 53c, and 53d are shown, the numbers of channels are merely exemplary, and embodiments of the device having different numbers of channels are considered to fall within the scope of the invention. Similarly, the number of barbs 54a, 54b, 54c, etc., attached to balloon 51 maybe varied.

Figure 6:
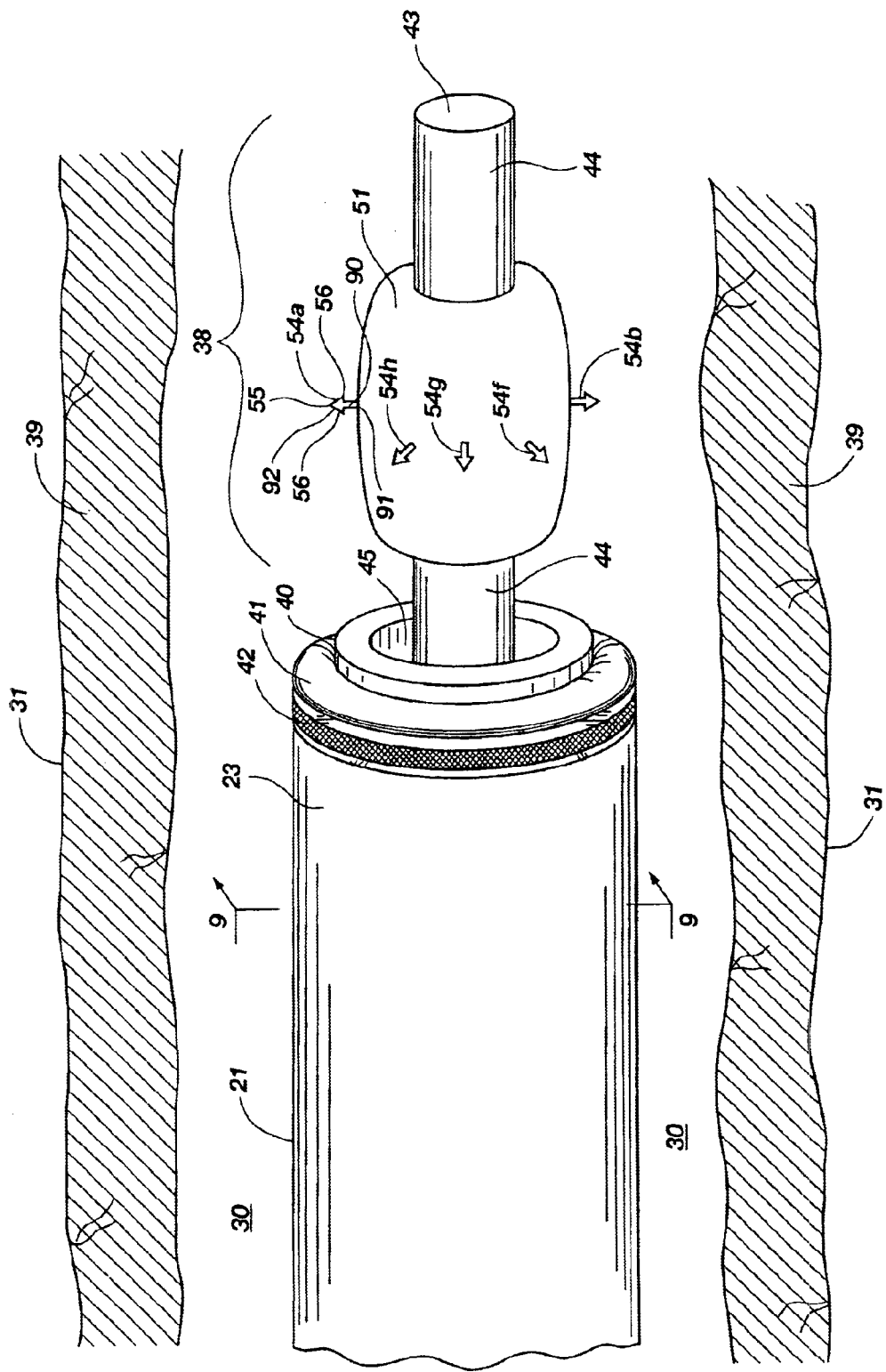
FIG. 6 a perspective view of the device of FIGS. 2 through 5, showing the balloon deflated and catheter extended.

FIG. 6, which depicts grasper shaft 44 extended out of the distal end 23 of tubular element 21, more clearly shows the shape of balloon 51. Balloon 51 is generally cylindrical in shape, with its inner surface attached to the exterior of grasper shaft 44. A plurality of barbs 54a, 54b, 54c, etc., are attached to the exterior of balloon 51. As noted previously, when balloon 51 is inflated so that its outer diameter is substantially equal to the diameter of lumen 30 of fallopian tube 31, barbs 54a, 54b, 54c, etc. are forced into fallopian tube wall 39. Each barb has a shaft 90 that is attached to the exterior of balloon 51 at a first end 91 and which has a tip 55 at second end 92 which allows it to be readily pushed into the tissue of fallopian tube wall 39. Backward extending points 56 are attached at or near tip 55 and extend back toward first end 91 of shaft 90, and serve to engage the tissue to prevent withdrawal of the barb from the fallopian tube wall 39. These features are specifically pointed out on barb 54a, but all barbs 54a, 54b, 54c, etc. include these features. The combination of balloon 51 and barbs 54a, 54b, 54c, etc. and grasper shaft 44 function together as grasper 38.

Figure 7:
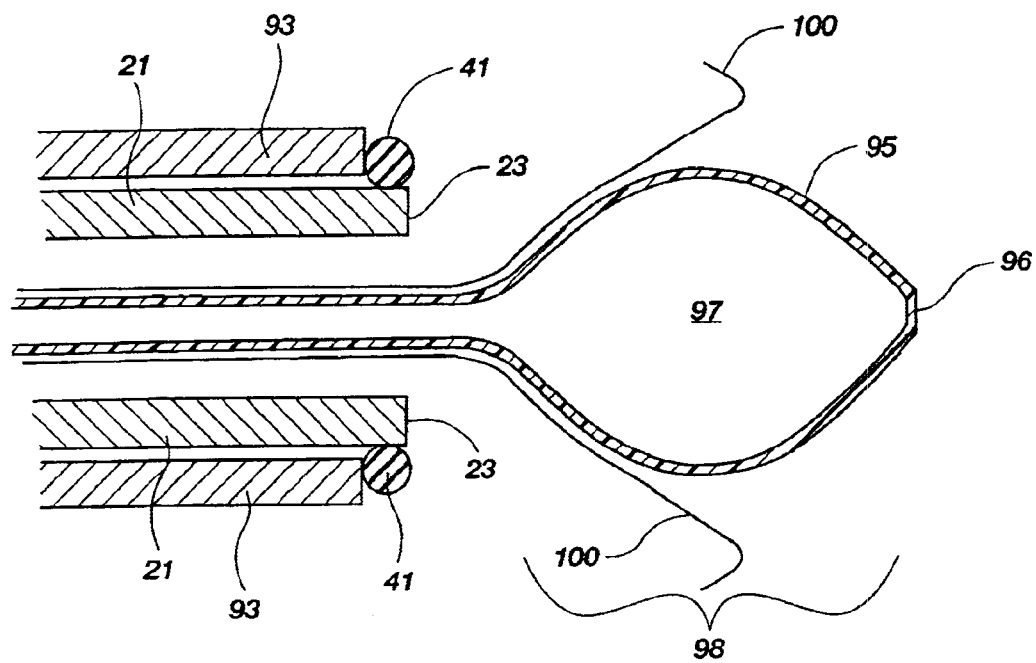
FIG. 7 is a longitudinal cross section view of an alternative embodiment of the device.

FIG. 7 depicts a further alternative embodiment of the invention in which ligating band 41 is pushed off of distal end 23 of tubular element 21 by sleeve 93, which is a tubular sleeve that is slidably disposed around tubular element 21 and can be slid distally to push ligating band 41 off of tubular element 21. In this and the other embodiments shown herein, ligating band 41 is released by being pushed off of distal end 23 of tubular element 21. However, the invention is not limited to embodiments in which the ligating band or other ligating structure is released by being pushed. Other mechanisms for releasing a ligating structure may be devised, for example, tubular element 21 could be retracted within sleeve 93, so that ligating band 41 is maintained in place while tubular element 21 is withdrawn from under it, thus allowing the ligating band to contract onto a grasped tissue bundle. Further, other means for holding a ligating band or other ligating structure at the end of tubular element 21 and then releasing it onto the grasped tissue bundle may be devised and are considered to fall within the scope of the invention.

The embodiment of the invention shown in FIG. 7 also shows an alternative version of grasper 38, in which the elongated catheter formed by grasper shaft 44 and balloon 51, as shown in FIGS. 3, 5 and 6, is replaced by an elongated catheter comprising inflatable catheter 95, which has a closed end 96 and interior lumen 97. Inflatable catheter 95 is formed of a pliable material that is sufficiently elastic that when the pressure of the fluid in interior lumen 97 is increased, inflatable catheter 95 inflates or balloons out at end region 98. When the pressure of the fluid in interior lumen 97 is reduced, end region 98 of inflatable catheter 95 returns to its original diameter. Inflatable catheter 97 is substantially functionally equivalent to the combination of grasper shaft 44 and balloon 51 as shown in FIGS. 3, 5 and 6.

Also shown in FIG. 7 are hooked wires 100, which provide an alternative hooking structure to the barbs used in the embodiment of FIGS. 3, 5, and 6. Two can be seen in the cross section, but a plurality of hooks (for example, four or five) would be used. When inflatable catheter 95 is uninflated, hooked wires 100 conform to the exterior of inflatable catheter 95, so inflatable catheter 95 and hooked wires 100 fit inside tubular element 21. When inflatable catheter 95 is inflated, hooked wires 100 are splayed outward to be pushed into and grasp the inner wall of the fallopian tube (not shown). When inflatable catheter 95 is deflated, hooked wires 100 return to their original position.

Figure 8:
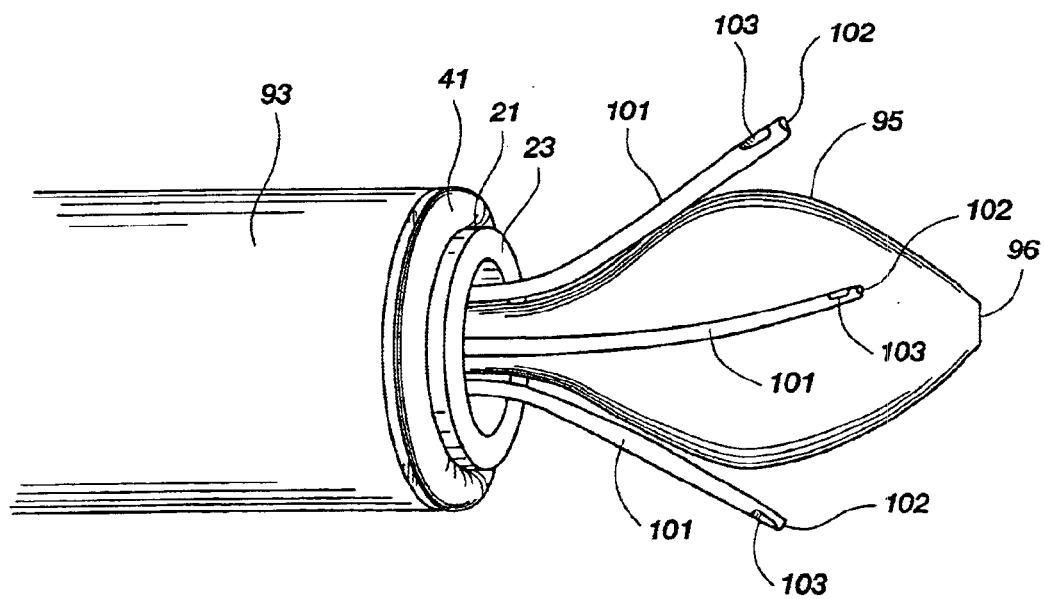
FIG. 8 is a perspective view of an embodiment of the device utilizing suction tubes as graspers.

A further alternative grasper 38 is shown in FIG. 8. Inflatable catheter 95 is as shown in FIG. 7, as is sleeve 93. Hooked wires 100 shown in FIG. 7 are replaced by suction tubes 101, each of which has an opening at or near its tip 102. In FIG. 8, openings 103 are positioned laterally, and tip 102 is closed. When inflatable catheter 95 is inflated, suction tubes 101 are urged outward to contact the wall of the fallopian tube (not shown). Generation of a vacuum in suction tubes 101, from an external vacuum source connected to device 20 at control segment 24 and communicating with suction tubes 101, causes suction tubes 101 to grasp the fallopian tube by drawing the tissue of the fallopian tube to opening 103 and holding it there for as long as the vacuum is maintained.

Figure 9:
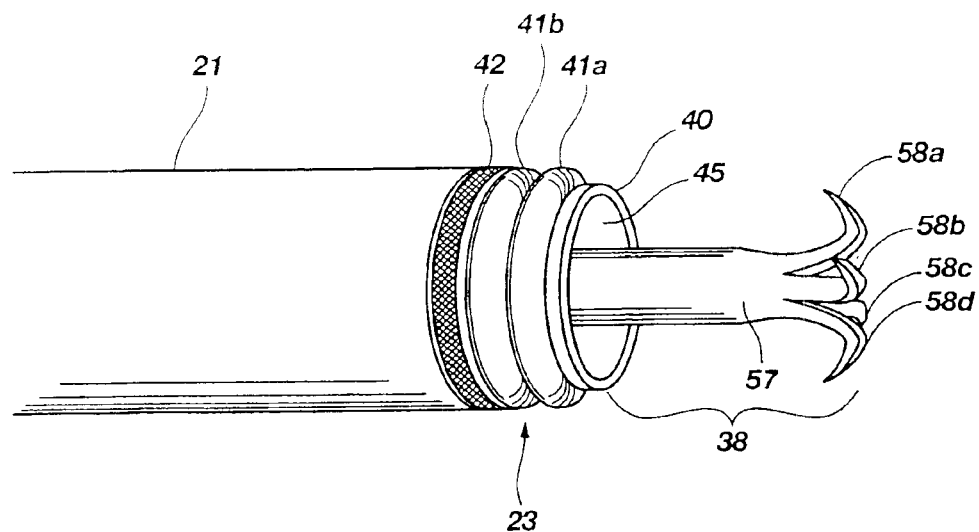
FIG. 9 depicts an alternative embodiment of the device tip having two o-rings carried on the device and an alternative grasper.
Figure 10:
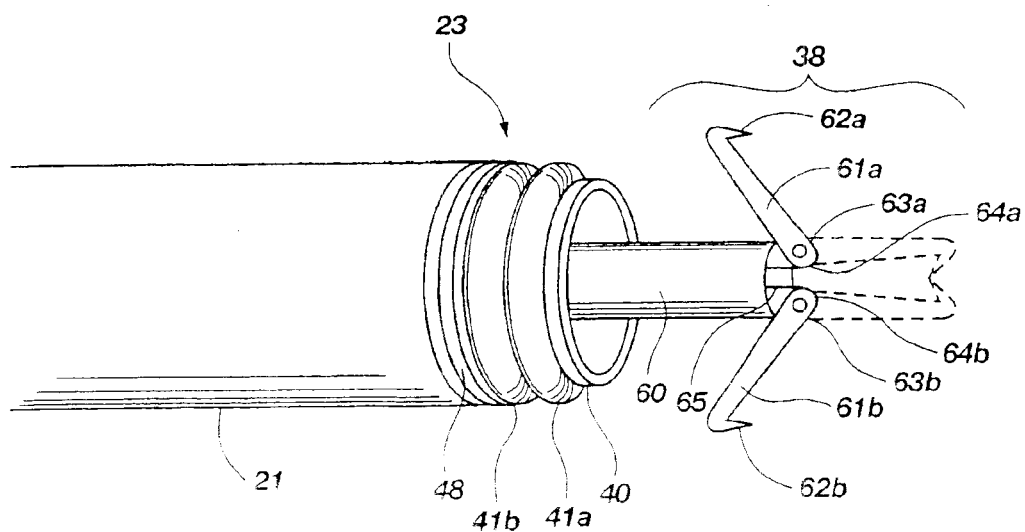
FIG. 10 depicts a further alternative embodiment of the device tip having two O-rings carried on the device and another alternative grasper.

The inventive device may be constructed with various other alternative grasper mechanisms. For example, a forceps-like mechanism could be used to grasp tissue in the interior of the fallopian tube, or other grasper mechanisms, for example, as shown in FIGS. 9 and 10, could be used. In FIG. 9, grasper 38 includes a grasper shaft 57 having a plurality of hooks 58a, 58b, 58c, and 58d. In this embodiment of the invention, grasping is accomplished when one or more of hooks 58a, 58b, 58c, and 58d catch on the wall of the fallopian tube. In the alternative embodiment of the invention shown in FIG. 110, grasper 38 includes grasper shaft 60 and a plurality of pivoting hooks 61a and 61b having angled points 62a and 62b. Pivoting hooks 61a and 61b would be held in a closed position (shown in dashed lines) while grasper 38 was in its retracted position in lumen 45 of tubular element 21, but when grasper 38 was extended, pivoting hooks 61a and 61b would be moved to their open position (shown in solid lines) and then closed again to grasp tissue on the interior of the fallopian tube. Pivoting hooks 61a and 61b pivot on pivot points 63a and 63b, actuated by actuation mechanisms 64a and 64b located in the lumen 65 of grasper shaft 60. Actuation mechanisms 64a and 64b could be, for example, drive rods which pass through grasper shaft 60 to control segment 24, where they are moved by a lever or trigger mechanism.

FIGS. 9 and 10 illustrate another variation in the design of the device, as well. More than one ligating band may be held at distal end 23 of tubular element 21, on lip 40 or in some other manner. In FIGS. 9 and 10, two ligating bands 41a and 41b are shown, but a larger number could be used as well. As will be described below, by providing two ligating bands 41a and 41b, it is possible to make two ligations in a fallopian tube, in order to provide more reliable blockage of the tube. In order to release ligating bands 41a and 41b in sequence, pusher balloon 42 (in FIG. 9) or pusher disk 48 (in FIG. 10) must be extended a first distance sufficient to push ligating band 41a off lip 40, and then be extended a second distance sufficient to push ligating band 41b off lip 40. Pusher balloon 42 would be expanded to a first volume, and then to a second, larger volume in order to push the two ligating bands sequentially. Similarly, pusher disk 48 would be extended to two different positions sufficient to release ligating bands 41a and 41b sequentially. It would be possible to use the two ligating bands to perform ligation of the two fallopian tubes sequentially, with the same device, but this is not preferred, because the withdrawal of the device from one fallopian tube, followed by reinsertion of the device into the second fallopian tube, provides an opportunity for contamination of the device and introduction of contaminants or infectious agents into the uterus or second fallopian tube.

It may be desirable to infuse antibiotics, topical anesthetics, or other drugs into the area of the ligation. Referring back to FIG. 2, drugs can be infused from the tip 23 of tubular element 21 into fallopian tube 31. One or more drug delivery lumens may be provided. For example, lumen 45 of tubular element 21 may function as a drug delivery lumen. Alternatively, one or more drug delivery lumens may be provided in the wall of tubular element 21, comparable to channels 46a and 46b shown in FIG. 5. As a further alternative, a drug delivery lumen may be provided by adding a second tubular element surrounding, and coaxial with tubular element 21, thereby forming a drug delivery lumen between tubular element 21 and the second tubular element. Drugs would be injected into the drug delivery lumen via access port 37, shown in FIG. 1, which would be connected to the drug delivery lumen.

If desired, an electrical current may be passed through grasper 38 to cauterize the grasped tissue. For example, current could be passed through barbs 54a, 54b, 54c, etc. of the device of FIGS. 2–6, hooked wires 100 of the device of FIG. 7, or through hooks 58a, 58b, 58c, 58d or 61a, 61b, etc. of the grasper as shown in FIGS. 9 and 10. Cauterization of tissue may be of use to reduce bleeding and to burn away small amounts of tissue to facilitate freeing of the fallopian tube from grasper 38. Cauterization of tissue may also be accomplished by delivery of a chemical cauterizing agent through a drug delivery lumen as discussed above.

The method of using the inventive device includes the following steps, described in the context of ligation of a fallopian tube, but applicable to the ligation of other tubular anatomical structures, as well. In the discussion of the method's steps, specific reference is made to the embodiment of the invention shown in FIGS. 1–3, 5 and 6, but the steps may be readily generalized to other embodiments of the invention.

1) Insertion of device. The first step is the insertion of the device into the fallopian tube, as shown in FIGS. 1–3. The grasper 38 is maintained in the unextended position within tubular element 21 during the insertion step in order to prevent damage to the components of grasper 38 and to facilitate insertion of the device by having the relatively smooth, readily inserted distal end 23 of tubular element 21 leading during insertion. Referring now to FIG. 1, a person performing the procedure holds device 20 by control segment 24 and inserts distal end 23 into the vagina 32 of the patient, and then into the lumen 33 of the uterus 34. Distal end 23 is then guided into a uterine horn 35 and into the lumen 30 of fallopian tube 31. Correct placement of distal end 23 may be determined by monitoring the length of tubular element 21 inserted after distal end 23 has passed the uterine horn 35 and entered the fallopian tube 31, as determined by change in resistance to insertion. Insertion of tubular element 21 into uterus 34 and fallopian tube 31 may also be performed with hysteroscopic guidance. Device 20 may include control wires (not shown) for steering distal end 23, or other steering methods utilized with catheters, with steering control 25 on control segment 24 used for steering distal end 23 during insertion.

Figure 11:
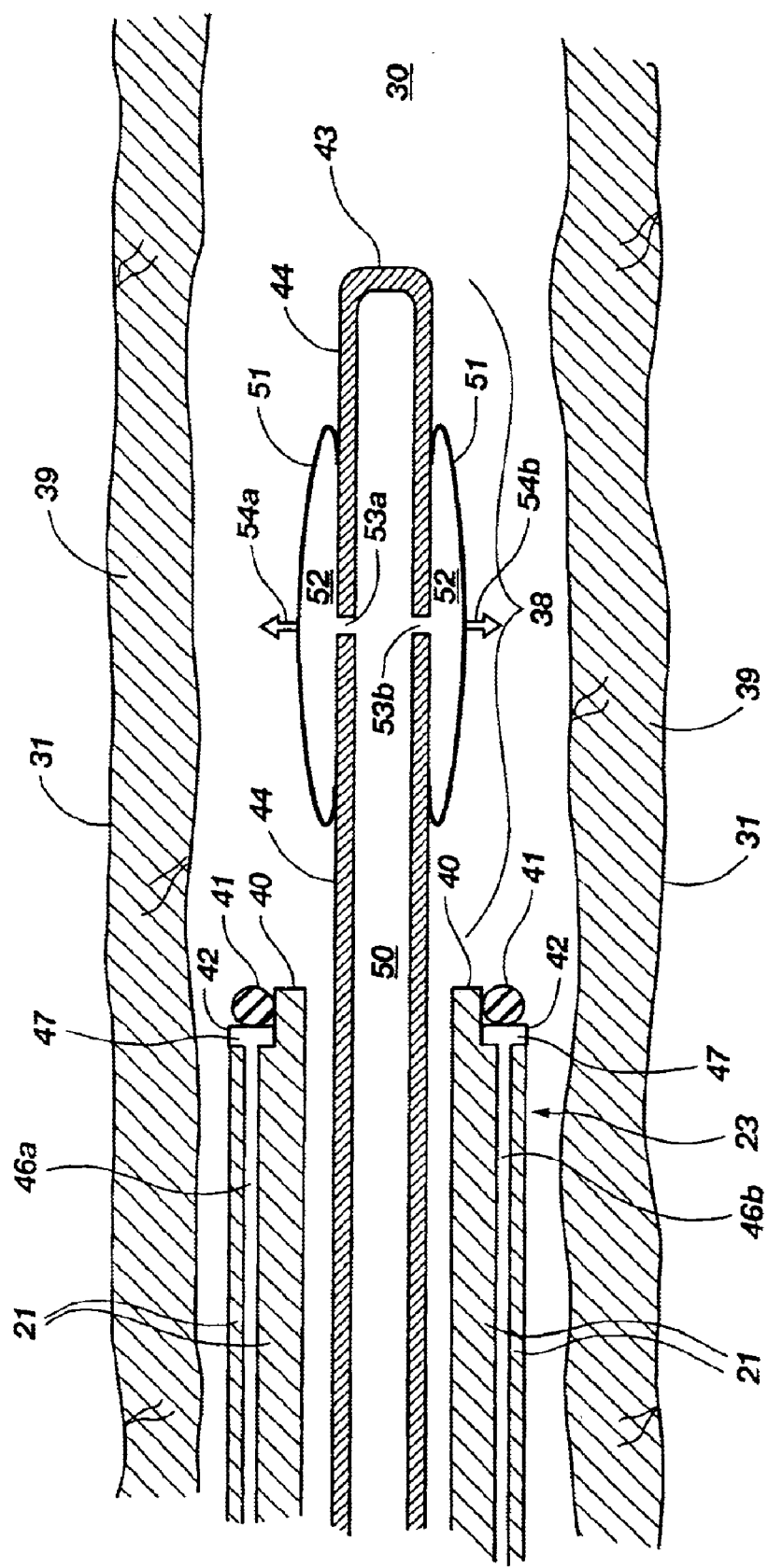
FIG. 11 is a longitudinal cross-sectional view taken along line 9—9 in FIG. 6.

2) Extension of grasper. As shown in FIGS. 6 and 11, once the distal end 23 of tubular element 21 has been positioned properly within the fallopian tube 31, grasper 38 is extended out of tubular element 21. Grasper 38 is thus passed through the central opening of ligating band 41. FIG. 11 is a cross-section of the device, taken along section line 9—9 in FIG. 6. Extension and retraction of grasper shaft 44 may be controlled by extension control 26 on control segment 24 in FIG. 1 which may be, for example, a trigger causing movement of a mechanical linkage. Various mechanisms may be devised for causing grasper shaft 44 to extend out of tubular element 21 by a predetermined distance, and the practice of the invention is not limited to a particular mechanism.

Figure 12:
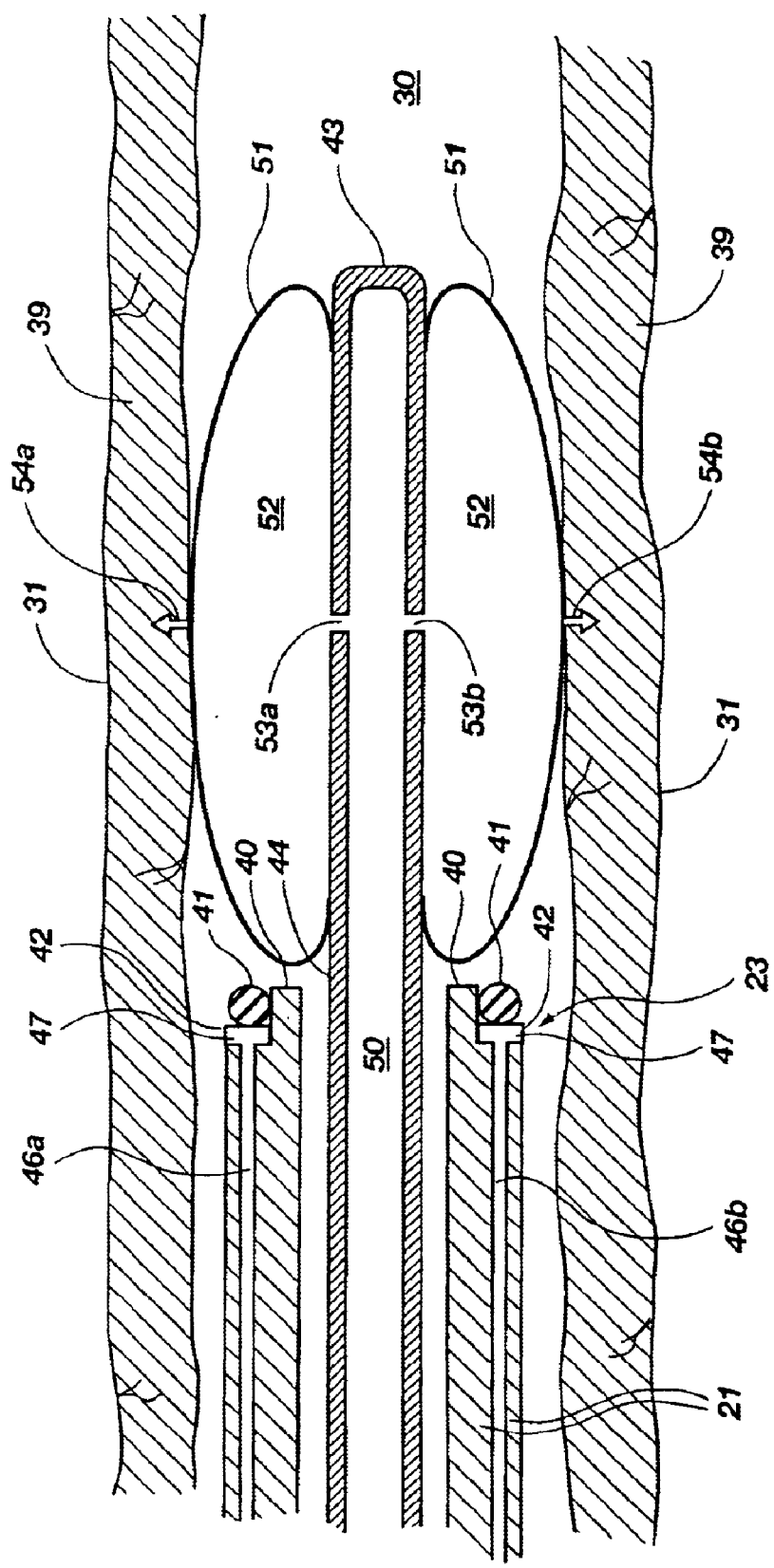
FIG. 12 is a longitudinal cross-sectional view of the device shown in FIGS. 2–7, depicting inflation of the balloon to force the barbs into the wall of the fallopian tube.

3) Grasping of tissue. Once grasper 38 has been extended out of tubular element 21, grasper 38 is activated to grasp tissue on the interior of fallopian tube wall 39. Control segment 24, shown in FIG. 1, may include a grasp control 27 for controlling grasping. As shown in FIG. 12, balloon 51 is inflated by fluid flowing through grasper shaft 44 until the outer diameter of balloon 51 is substantially as large as the inner diameter of fallopian tube 31. Barbs 54a, 54b, etc. are then pushed into and grasp or engage fallopian tube wall 39. Naturally, grasping of tissue could also be accomplished with an alternative grasper mechanism, such as those shown in FIGS. 7, 8, 9 and 10.

Figure 13:
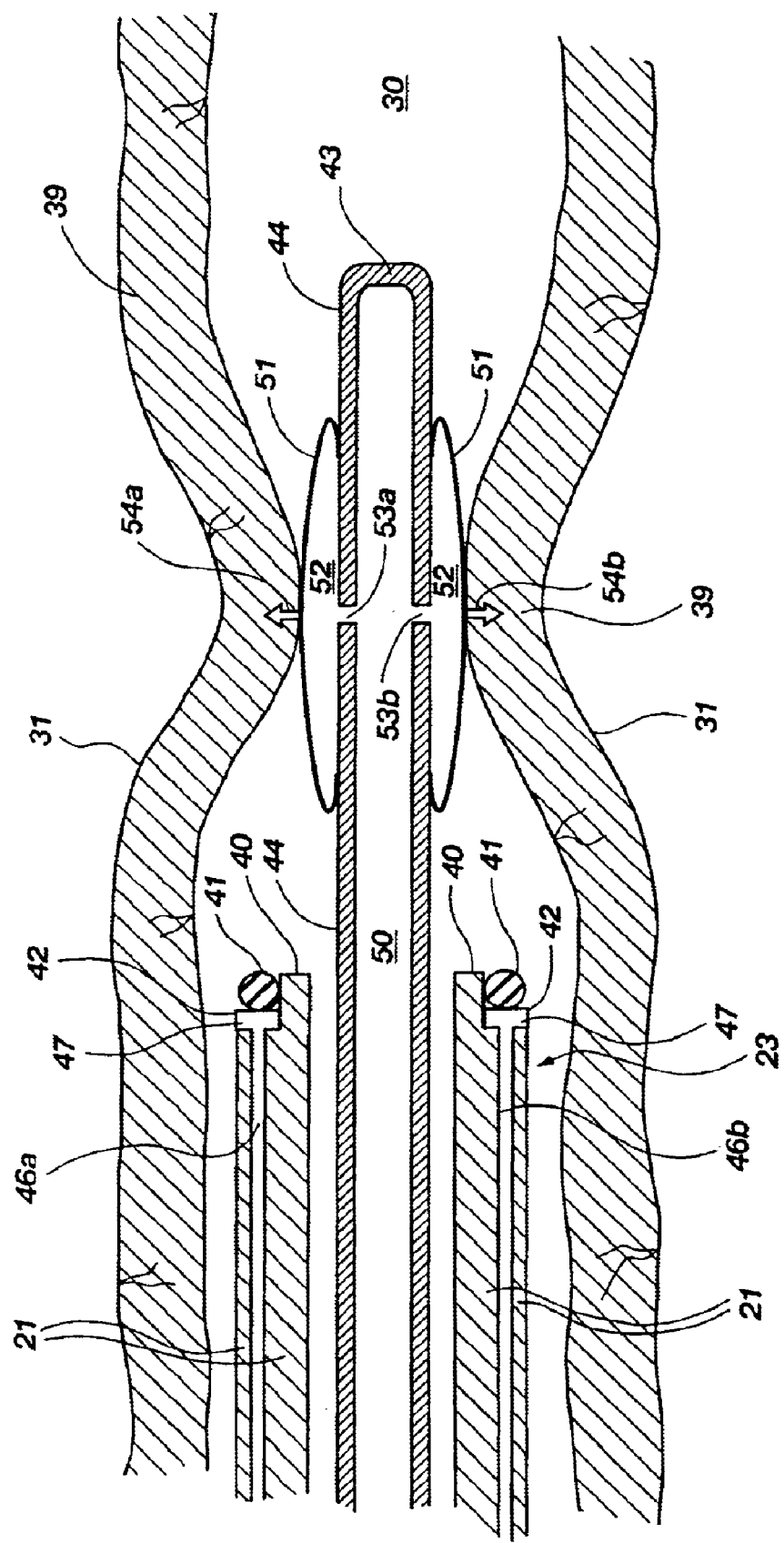
FIG. 13 is a longitudinal cross-sectional view of the device showing deflation of the balloon to draw the wall of the fallopian tube radially inward.
Figure 14:
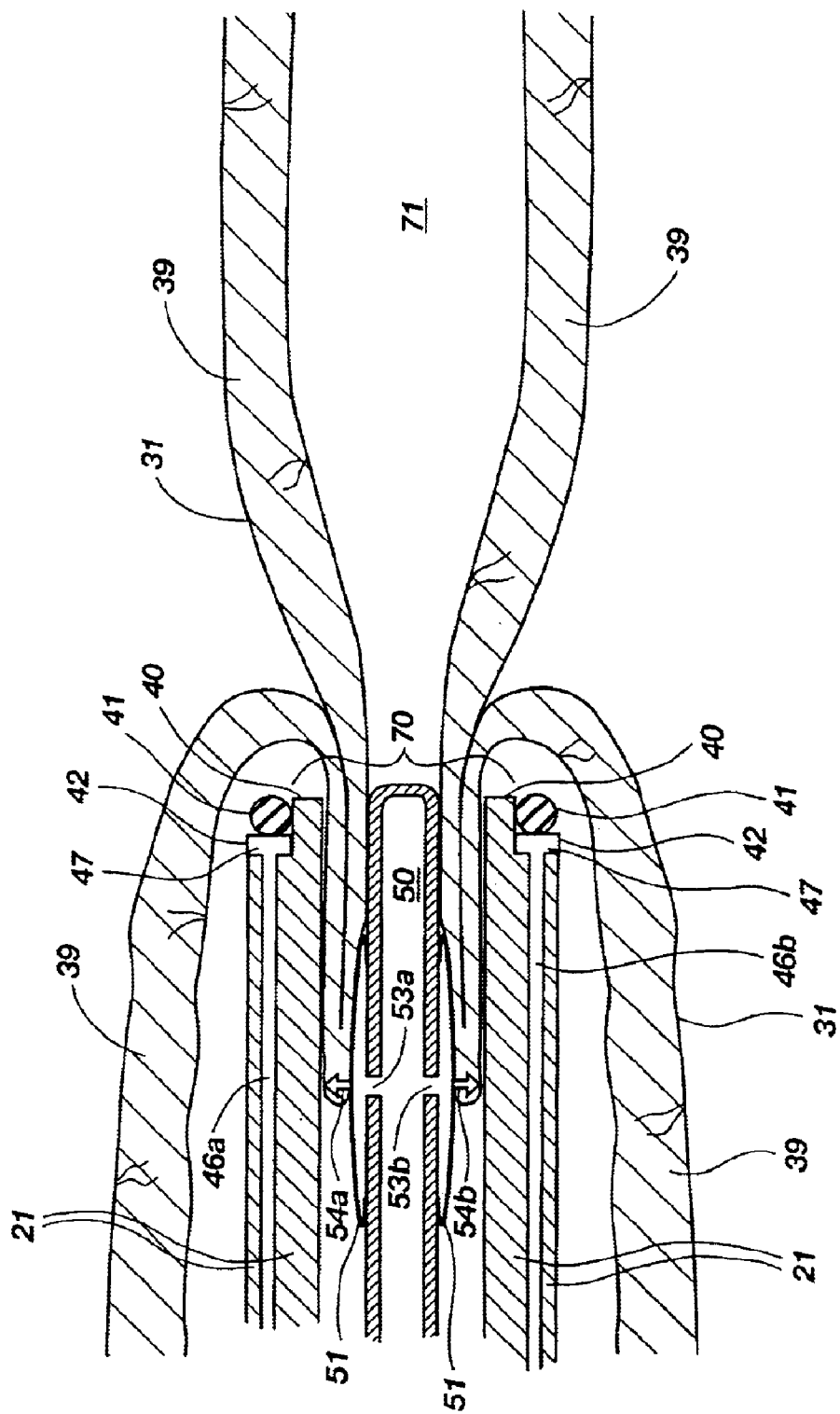
FIG. 14 is a longitudinal cross-sectional view of the device showing retraction of the grasper into the outer tube, drawing a fold of the fallopian tube with it into the outer tube.

4) Retraction of grasper shaft and grasped tissue. As shown in FIG. 13, once tissue has been grasped by barbs 54a, 54b, etc., balloon 51 is deflated, drawing the fallopian tube wall 39 radially inward toward grasper shaft 44. Referring now to FIG. 14, following deflation of balloon 51, grasper 38 is retracted into distal end 23 of tubular element 21. A tissue bundle 70 from the fallopian tube wall 39, is drawn into distal end 23 of tubular element 21 by grasper 38. When tissue bundle 70 is drawn into distal end 23 of tubular element 21, it is at the same time drawn through the central opening of ligating band 41.

Figure 15:
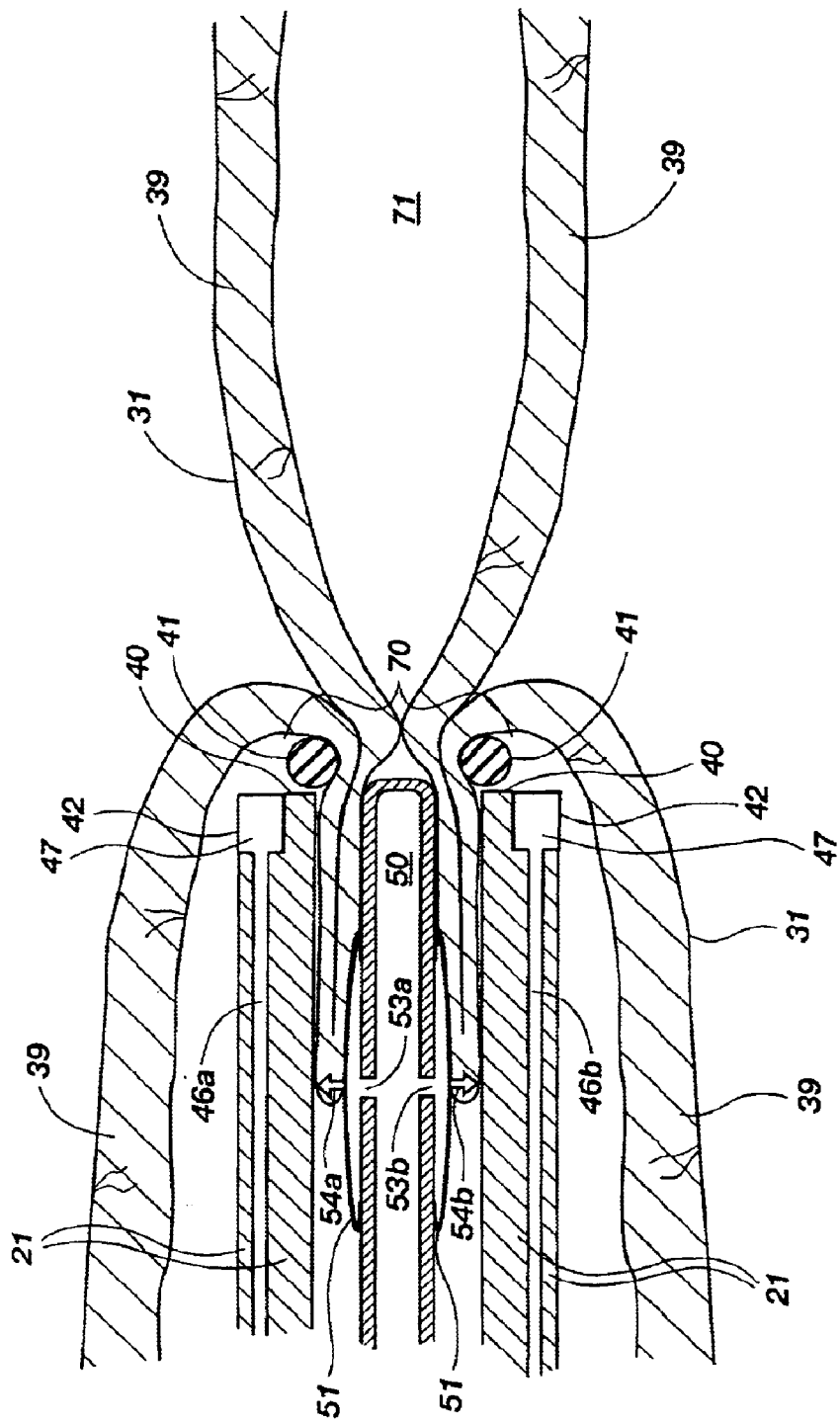
FIG. 15 is a longitudinal cross-sectional view of the device showing expansion of the pusher balloon to push the ligating band off the end of the outer tube and onto the fold of fallopian tube.

5) Releasing of ligating band onto tissue bundle. As shown in FIG. 15, ligating band 41 is pushed off of lip 40 by the expansion of pusher balloon 42. Pusher balloon 42 may be expanded by air or liquid, such as water or saline solution, forced into pusher balloon 42 via channels 46a and 46b. Once pushed off of lip 40, ligating band 41 contracts around tissue bundle 70. An alternative release mechanism, such as the pusher mechanisms shown in FIG. 4 or 7, could be used at this step, instead. The pusher mechanism may be controlled by a push controller 28 located on control segment 24 in FIG. 1.

If tissue bundle 70 includes tissue from around the circumference of the tubular anatomical structure, application of ligating band 41 to tissue bundle 70 will produce blockage of fallopian tube 31. If, on the other hand, tissue bundle 70 includes tissue from only one side of the fallopian tube 31, ligation of tissue bundle 70 will only separate tissue bundle 70 from the remainder of fallopian tube 31, but not block fallopian tube 31. This may be desirable in certain medical applications, such as ligating damaged or cancerous tissue, but of course would not be effective for contraception. A grasper which grasps tissue around the circumference of the tube will form a tissue bundle 70 that includes tissue from around the circumference of the tube. It may also be possible to form a tissue bundle that includes tissue from around the circumference of the tube by grasping tissue around only a part of the circumference of the tube, if the amount of tissue grasped is large enough that the stiffness of the tube causes the entire circumference of the tube to fold in to form the tissue bundle.

6) Freeing of grasped tissue. Following application of a ligating band or bands, tissue bundle 70 must be freed from grasper 38. This may be accomplished by simply tearing barbs 54a, 54b, etc. from tissue bundle 70. Since tissue bundle 70 is separated from the main portion of the fallopian tube by the ligation, tissue damage caused by tearing out of the barbs is not of great concern. Cauterization of the tissue by passing current through the barbs, hooks, or other portion of the grasper contacting the tissue, or by delivering a chemical cauterizing agent, may facilitate freeing of tissue and reduce bleeding.

Figure 16:
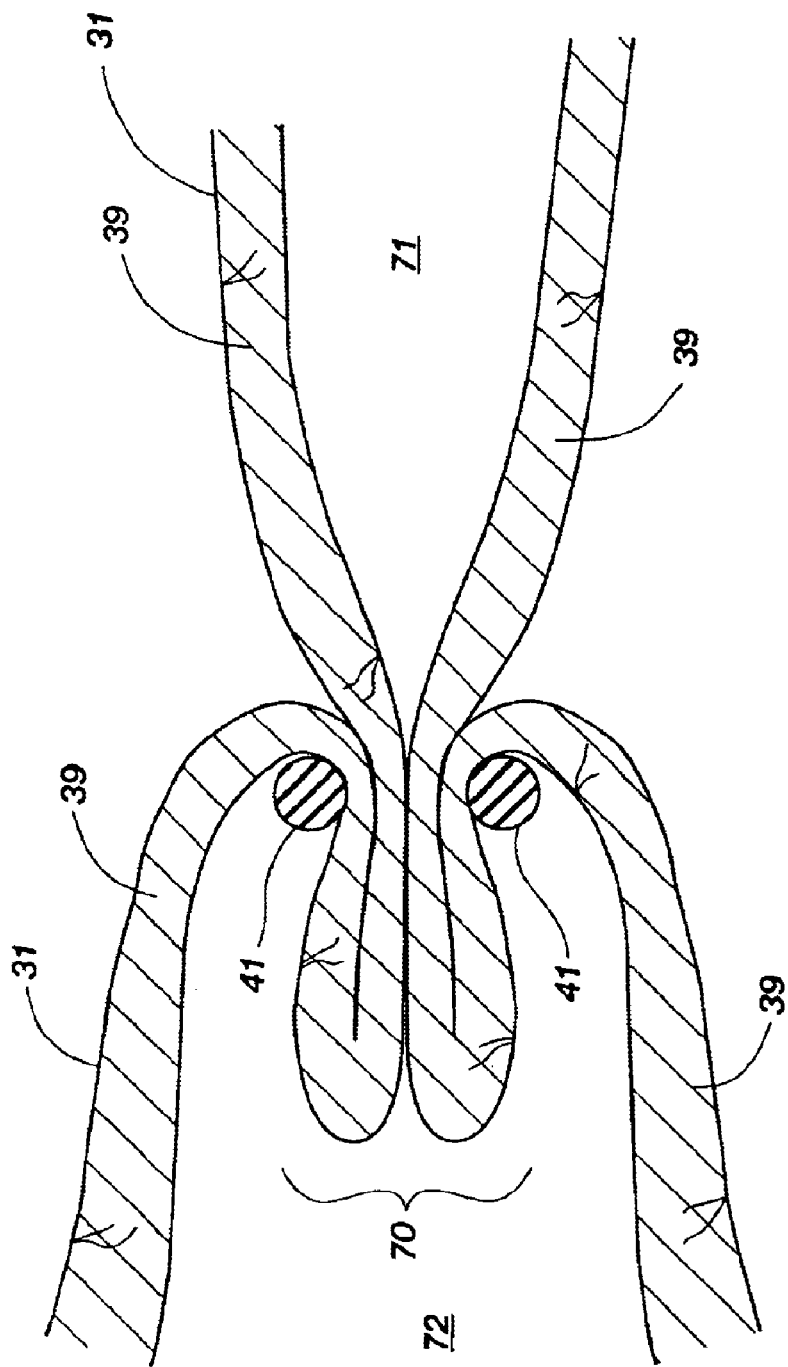
FIG. 16 is a longitudinal cross-sectional view of the ligated fallopian tube.

7) Withdrawal of device. Following ligation of tissue bundle 70 by ligating band 41, and freeing of tissue bundle 70 from grasper 38, the device may be withdrawn. FIG. 16 shows the ligated fallopian tube 31, with tissue bundle 70 secured by ligating band 41. The lumen of fallopian tube 31 is now divided into two sections separated by the ligation: distal lumen 71, on the side closer to the ovary; and proximal lumen 72, on the side closer to the uterus. If it is desired that only a single ligating band be applied to the fallopian tube, the device is now withdrawn completely from the fallopian tube.

Figure 17:
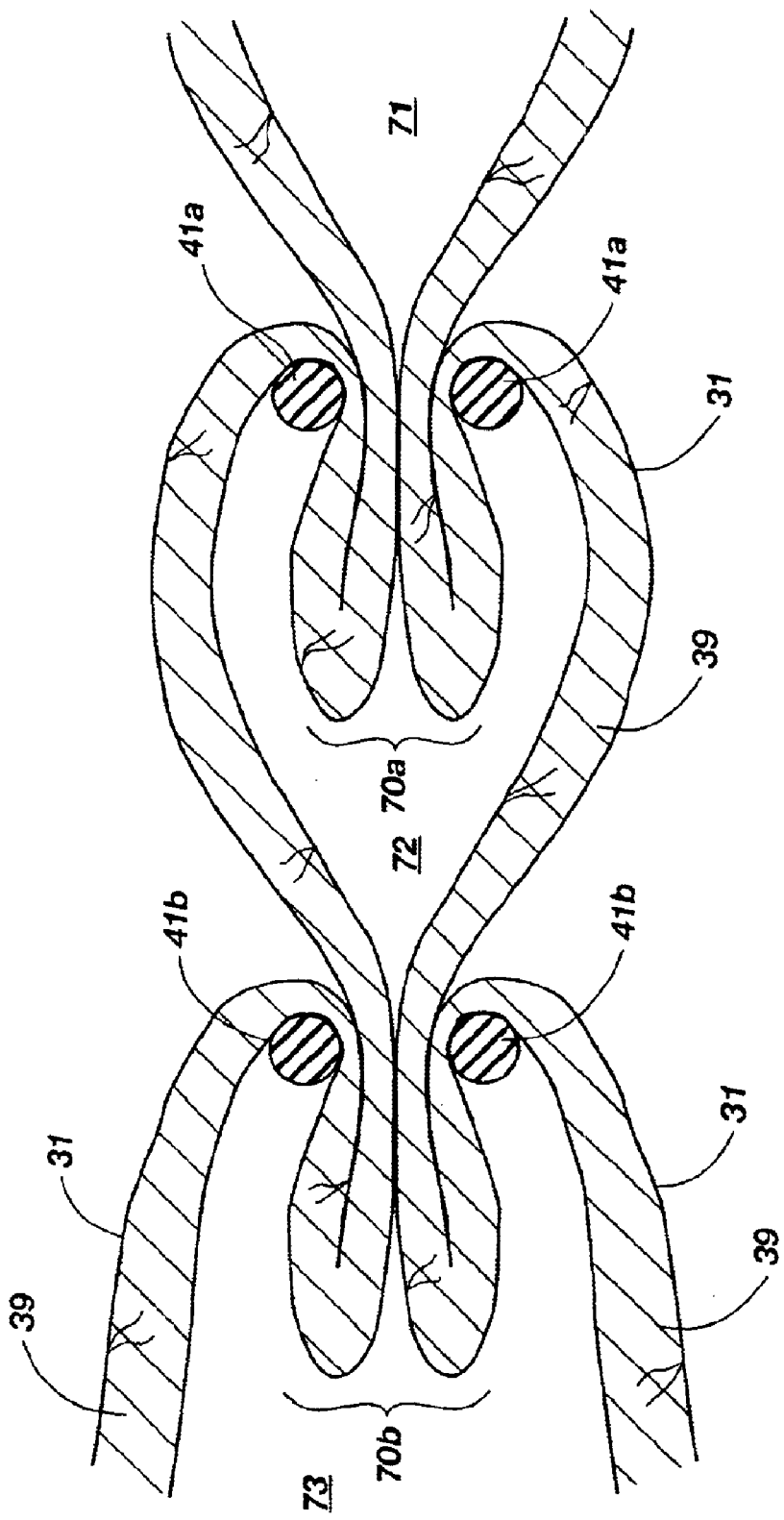
FIG. 17 is a longitudinal cross-sectional view of the fallopian tube following application of a second ligating band.

8) Application of additional ligating bands. Referring now to FIG. 17, if it is desired that more than one ligating band be applied to the fallopian tube, after the application of first ligating band 41a to first tissue bundle 70a, tubular element 21 is withdrawn only partially, to a new, more proximal position within the fallopian tube, and steps 2 through 5 are repeated at the new, more proximal position, to apply second ligating band 41b to second tissue bundle 70b to produce a double ligation. Lumen 72 is now between the first and second ligations, and lumen 73 is located most proximally on the side closer to the uterus. Steps 6 through 8 may be repeated as many times as desired to apply multiple ligating bands to one fallopian tube; however, it is anticipated that reliable ligation would be provided by one to three ligating bands, and larger numbers of ligating bands would not be necessary or desirable.

In order to accomplish sterilization, it is of course necessary to ligate both fallopian tubes. Thus the procedure would be repeated for the second tube in a similar manner. As noted above, it is preferred that the same device not be withdrawn from the first fallopian tube and then reinserted into the second fallopian tube, due to the risk of infection. Therefore, two sterilized devices are preferably provided in order to perform ligation of both fallopian tubes. It would be possible to manufacture the device having some or all components being disposable.

While the present invention has been described and illustrated in terms of certain specific embodiments, those of ordinary skill in the art will understand and appreciate that it is not limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. A method of blocking a tubular anatomical structure, comprising the steps of:

grasping tissue with an inflatable member on the interior of said tubular anatomical structure at one or more locations disposed along a lumen of said tubular anatomical structure and manipulating said tubular anatomical structure to form an inverted folded tissue bundle comprising tissue from around the circumference of said tubular anatomical structure; and applying a ligating structure to said tissue bundle.

2. The method of claim 1, wherein said tubular anatomical structure is a fallopian tube.

3. The method of claim 1, wherein said ligating structure is a ligating band.

4. The method of claim 1, comprising the further steps of:

grasping tissue on the interior of said tubular anatomical structure at a second location to form a second tissue bundle comprising tissue from around the circumference of said tubular anatomical structure; and applying a second ligating structure to said second tissue bundle.

5. A method of ligating a tubular anatomical structure having a wall surrounding a central lumen, comprising the steps of:

inserting a first end of an elongated tubular element into the lumen of the tubular anatomical structure, at least one ligating structure being secured at said first end of said tubular element;

extending a grasper out of said first end of said tubular element and through said at least one ligating structure;

grasping tissue from the wall of said tubular anatomical structure with said grasper at one or more locations around a circumference of, and disposed apart from an end of, said lumen, wherein said grasper comprises an inflatable end portion;

retracting said grasper into said first end of said tubular element, drawing the grasped tissue with said grasper into said first end of said tubular element and through said ligating structure to form an inverted tissue bundle within said first end of said tubular element; and releasing said at least one ligating structure from said first end of said tubular element to contract about said inverted tissue bundle to form a ligation of said tubular anatomical structure;

freeing said tissue bundle from said grasper; and withdrawing said tubular element from said tubular anatomical structure.

6. The method of claim 5, wherein said step of withdrawing comprises withdrawing said tubular element completely from said tubular anatomical structure.

7. The method of claim 5, wherein at least two ligating structures are secured at said first end of said tubular element, wherein said step of withdrawing comprises withdrawing said tubular element partially from said tubular anatomical structure to a new position within said tubular anatomical element, and wherein said method comprises the further step of:

repeating said steps of extending, retracting, releasing, freeing and withdrawing to form a second ligation of said tubular anatomical structure.

8. The method of claim 5, wherein said grasper comprises an elongated catheter having a plurality of hooking structures positioned about and capable of moving with said inflatable end portion, and wherein said step of grasping comprises:

inflating said inflatable end portion until at least a portion of said plurality of hooking structures are forced into said wall of said tubular anatomical structure to grasp tissue of said wall; and deflating said inflatable end portion until it is capable of fitting into said first end of said elongated tubular element.

9. The method of claim 8, wherein said step of freeing comprises passing electrical current through at least a portion of said plurality of hooking structures to cauterize the grasped tissue.

10. The method of claim 5, wherein said grasper comprises at least one suction tube having an opening, wherein said step of grasping comprises generating a vacuum in said suction tube sufficient to draw and hold tissue from the wall of said tubular anatomical structure against said opening, and wherein said freeing step comprises releasing said vacuum.

11. The method of claim 5, wherein said tubular anatomical structure is a fallopian tube.

12. A method of blocking a lumen of a tubular anatomical structure, comprising the steps of:

manipulating an inflatable member to grasp tissue on the interior of a stretch of said lumen;

folding said tubular anatomical structure inwardly upon itself to form an inverted tissue bundle comprising tissue from around a circumference of said lumen, said tissue bundle being disposed within said stretch of said lumen; and applying a ligating structure to said tissue bundle effective to block a passage through said lumen.

13. The method of claim 12, wherein:

said applying step comprises engaging a ligating band around said tissue bundle.

14. The method of claim 12, wherein:

said folding step comprises drawing said tissue bundle through an aperture formed in expansion structure adapted to hold said ligating structure in a dilated condition; and said applying step comprises releasing said ligating structure from engagement on said expansion structure.

* * * * *